United States Patent
Veliss et al.

(10) Patent No.: US 10,342,945 B2
(45) Date of Patent: Jul. 9, 2019

(54) RESPIRATORY MASK HAVING GAS WASHOUT VENT AND METHOD FOR MAKING THE MASK

(71) Applicant: ResMed Pty Ltd, Bella Vista (AU)

(72) Inventors: Lee James Veliss, Rotterdam (NL); Philip Thomas Stallard, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 1149 days.

(21) Appl. No.: 14/598,598

(22) Filed: Jan. 16, 2015

(65) Prior Publication Data
US 2015/0128950 A1    May 14, 2015

Related U.S. Application Data

(63) Continuation of application No. 11/793,001, filed as application No. PCT/AU2006/000036 on Jan. 12, 2006, now Pat. No. 8,967,146.
(Continued)

(51) Int. Cl.
*A61M 16/06*    (2006.01)
*A61M 16/08*    (2006.01)
*A61M 16/00*    (2006.01)

(52) U.S. Cl.
CPC .... *A61M 16/0622* (2014.02); *A61M 16/0066* (2013.01); *A61M 16/06* (2013.01);
(Continued)

(58) Field of Classification Search
CPC .......... A61M 16/0622; A61M 2205/42; A61M 16/0616; A61M 16/0066; A61M 16/0633; A61M 16/06
See application file for complete search history.

(56) References Cited

U.S. PATENT DOCUMENTS 2,831,487 A    4/1958    Tafilaw
3,104,736 A    9/1963    Ludlow et al.
(Continued)

FOREIGN PATENT DOCUMENTS

JP    2001-511035    8/2001
WO    WO 98/34665    8/1998
(Continued)

OTHER PUBLICATIONS

International Search Report for PCT/AU2006/000036 dated Mar. 3, 2006.
(Continued)

*Primary Examiner* — Timothy A Stanis
(74) *Attorney, Agent, or Firm* — Nixon & Vanderhye P.C.

(57) ABSTRACT

A washout vent for a mask for use with a system for supplying breathable gas pressurized above atmospheric pressure to an airway of a mammal for treatment of sleep disordered breathing, includes a solid mask section and a vent orifice extending through a thickness of the solid mask section and adapted for gas washout. The vent orifice includes opposed side walls providing a flow passage that allows gas to flow along the opposed side walls from an interior of the mask to atmosphere in use, and the opposed side walls defining at least a portion of a conic section having a length substantially greater than its width. The vent orifice includes an orifice inlet at the interior of the mask and an orifice exit open to atmosphere, and the opposed side walls converge from the orifice inlet to the orifice exit to reduce noise of gas washout.

51 Claims, 21 Drawing Sheets

Related U.S. Application Data

(60) Provisional application No. 60/643,114, filed on Jan. 12, 2005, provisional application No. 60/714,910, filed on Sep. 8, 2005.

(52) U.S. Cl.
CPC .... *A61M 16/0616* (2014.02); *A61M 16/0633* (2014.02); *A61M 16/0683* (2013.01); *A61M 16/0816* (2013.01); *A61M 16/0825* (2014.02); *A61M 2205/42* (2013.01)

(56) References Cited

U.S. PATENT DOCUMENTS

| | | |
|---|---|---|
| 3,732,948 A | 5/1973 | Benton et al. |
| 4,754,924 A | 7/1988 | Shannon |
| 5,560,354 A | 10/1996 | Berthon-Jones et al. |
| 5,988,160 A | 11/1999 | Foley et al. |
| 6,112,746 A | 9/2000 | Kwok et al. |
| 6,561,190 B1 | 5/2003 | Kwok |
| 6,561,191 B1 | 5/2003 | Kwok |
| 6,581,594 B1 | 6/2003 | Drew et al. |
| 6,644,316 B2 | 11/2003 | Bowman et al. |
| 6,668,830 B1 | 12/2003 | Hansen et al. |
| 6,691,707 B1 | 2/2004 | Gunaratnam et al. |
| 6,823,865 B2 | 11/2004 | Drew et al. |
| 7,011,090 B2 | 3/2006 | Drew et al. |
| 2001/0027787 A1 | 10/2001 | Reed |
| 2002/0153012 A1 | 10/2002 | Gunaratnam et al. |
| 2003/0005931 A1 | 1/2003 | Jaffre et al. |
| 2003/0079751 A1 | 5/2003 | Kwok |
| 2003/0196657 A1 | 10/2003 | Ging et al. |
| 2004/0094157 A1 | 5/2004 | Dantanarayana et al. |
| 2004/0226566 A1 | 11/2004 | Gunaratnam et al. |
| 2011/0180071 A1 | 7/2011 | Veliss et al. |

FOREIGN PATENT DOCUMENTS

| | | |
|---|---|---|
| WO | WO 00/78381 | 12/2001 |
| WO | WO 2004/022147 | 3/2004 |
| WO | WO 2004/096332 | 11/2004 |

OTHER PUBLICATIONS

International Preliminary Report on Patentability, PCT/AU2006/000036 (dated Jul. 17, 2007).
Office Action issued in corresponding Japanese Appln. No. 2007-550639 (dated Apr. 5, 2011).
Office Action issued in corresponding Australian Appln. No. 2006206043 (dated Aug. 25, 2010).
Extended European Search Report issued in European Appln. No. 06704772.0, dated Nov. 3, 2009.
Second Office Action issued in Chinese Appin. No. 200680001660.5 (dated Oct. 9, 2009) with English translation.

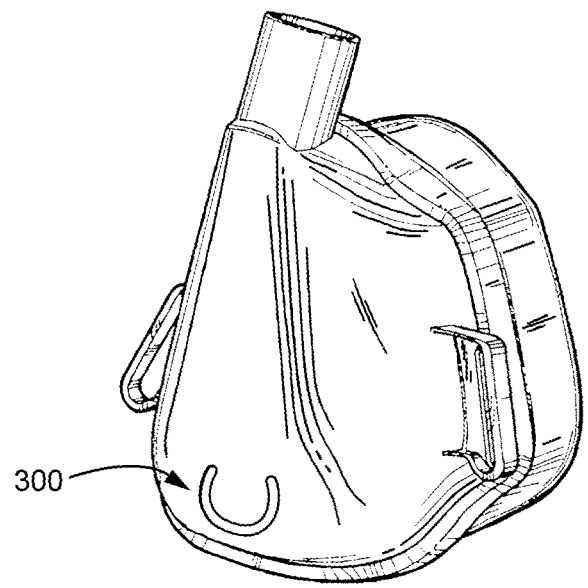
Fig. 23
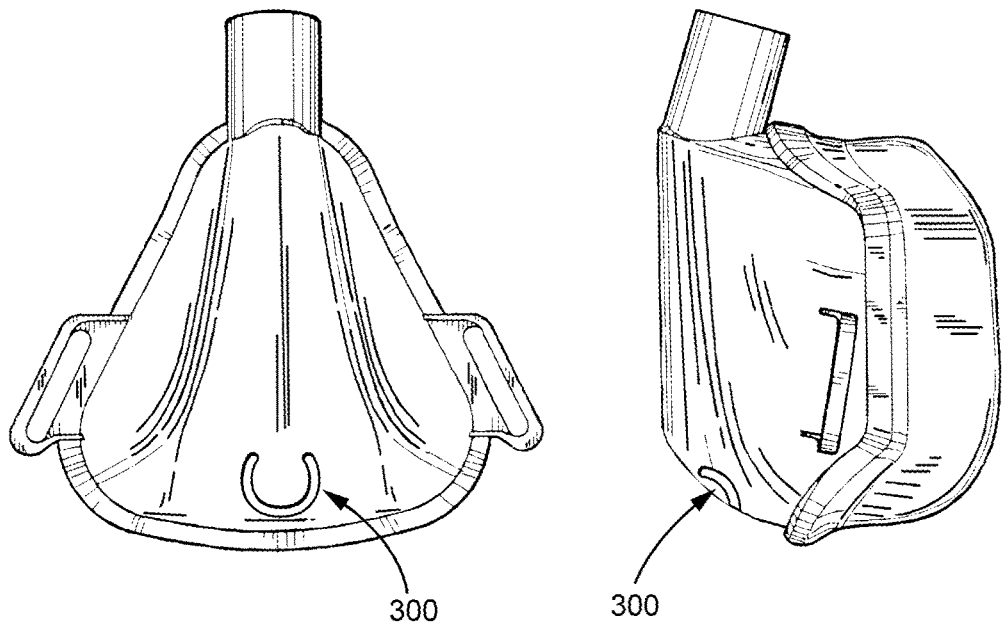
Fig. 24
Fig. 25

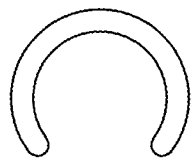
Fig. 28        Fig. 29
Fig. 30
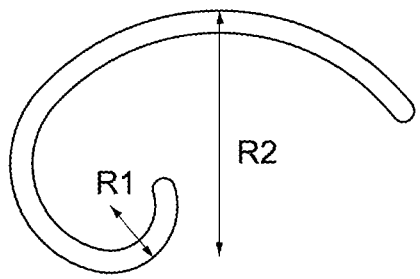
Fig. 31        Fig. 32
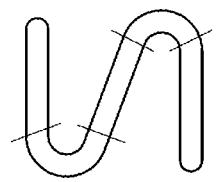
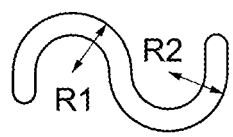
Fig. 33        Fig. 34

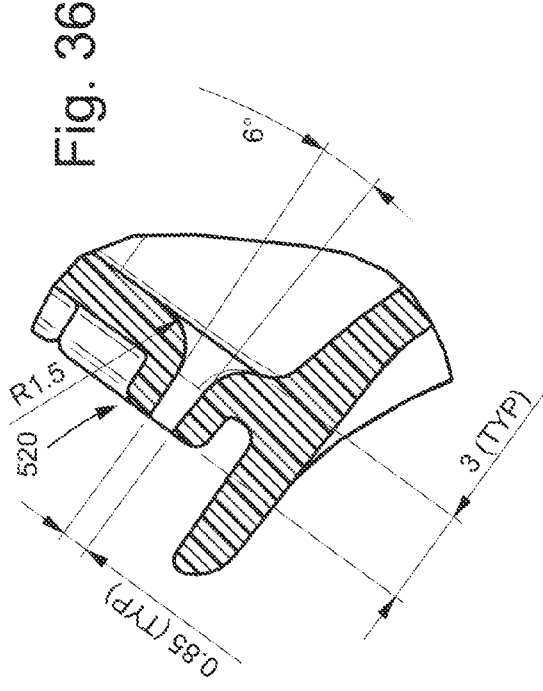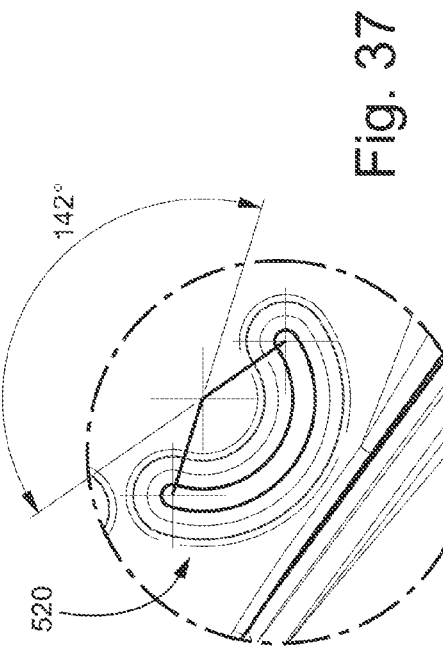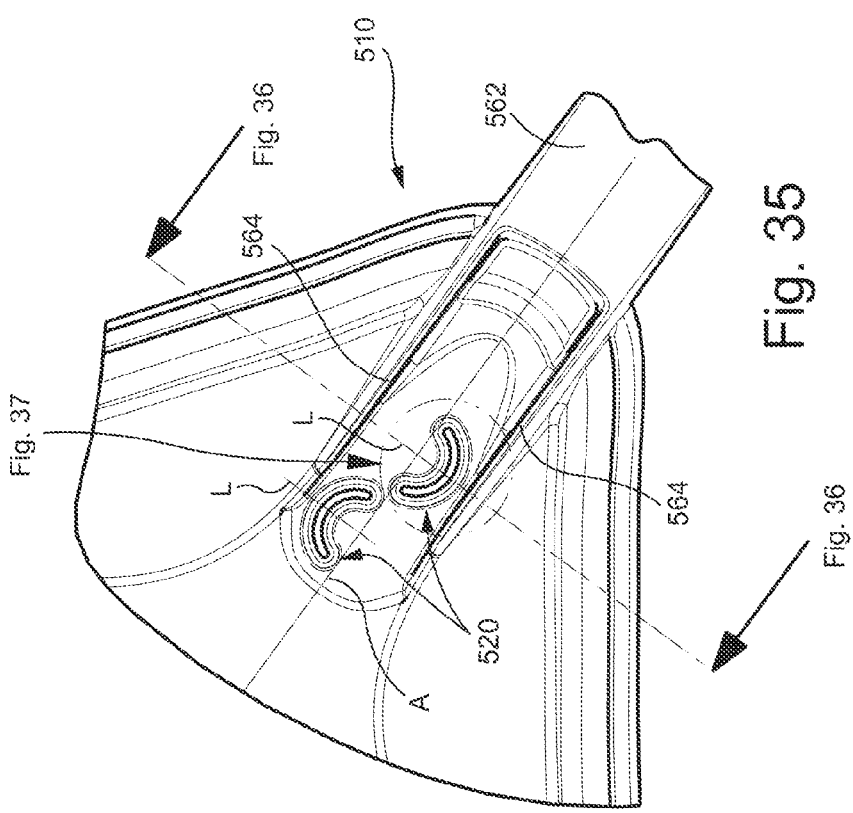

RESPIRATORY MASK HAVING GAS WASHOUT VENT AND METHOD FOR MAKING THE MASK

CROSS-REFERENCE TO APPLICATIONS

This application is a continuation of U.S. patent application Ser. No. 11/793,001, filed Mar. 17, 2010, which is the U.S. National Phase of International Patent Application No. PCT/AU2006/000036, filed Jan. 12 2006,which claims the benefit of U.S. Provisional Application Nos. 60/643,114, filed Jan. 12, 2005, and 60/714,910, filed Sep. 8, 2005, each of which is incorporated herein by reference in its entirety.

BACKGROUND OF THE INVENTION

Treatment of sleep disordered breathing (SDB), such as obstructive sleep apnea (OSA), by continuous positive airway pressure (CPAP) flow generator systems involves the continuous delivery of air (or other breathable gas) pressurized above atmospheric pressure to the airways of a human or other mammalian patient via a conduit and a mask. Typically, the mask fits over the mouth and/or nose of the patient. Pressurized air flows to the mask and to the airways of the patient via the nose and/or mouth. As the patient exhales, carbon dioxide gas may collect in the mask. A washout vent in the mask or conduit discharges the exhaled gas from the mask atmosphere.

The washout vent is normally located in the mask or near the mask in the gas delivery conduit coupled to the mask. The washout of gas through the vent to the atmosphere removes exhaled gases to prevent carbon dioxide build-up, and hence "rebreathing", which represent a health risk to the mask wearer. Adequate gas washout is achieved by selecting a vent size and configuration that allows a minimum safe washout flow at a low operating CPAP pressure, which typically can be as low as 4 cm $H_2O$ for adults and 2 cm $H_2O$ for children.

Noise is a significant issue in CPAP treatment for the patient and/or the patient's bed partner. Excessive noise can lead to patients being non-compliant with the CPAP therapy. One source of noise is the exhaust through the vent in the mask or conduit. The flow of gas through the vent creates noise as it exits to and interacts with the atmosphere. Noise can adversely affect patient and bed-partner comfort, depending on both the magnitude and character of the noise. Further, bi-level gas delivery regimes tend to generate more noise than do constant level gas delivery regimes. This is thought to be due to the extra turbulence created by the gas accelerating and decelerating as it cycles between relatively low and relatively high pressures in the bi-level gas delivery systems.

The washout vents may offer a generally fixed impedance to air flow (for example having a generally unchanging geometry with time) or a variable impedance. In a fixed vent design, the vent flow increases with mask pressure, such that the vent flow may be adequate at a low pressure and excessive at high pressure. The variations in flow through fixed vent can lead to noise. Fixed vents are generally simple and inexpensive to make and operate. A variable vent design could provide a constant or near constant vent flow across a range of mask pressures having the advantage that noise will not increase as mask pressure is increased. This may lead to lower vent flow at high pressures which may in turn lead to less noise. However variable vents suffer from difficulties in manufacture, assembly, consistency, cleaning and usability.

Fixed gas vents are known that have relatively low noise levels, which levels may be as low as 30 dBA at a therapy (mask) pressure of 12 cm $H_2O$. Such vents include, for example, the Resumed MIRAGE™ mask (disclosed in U.S. Pat. No. 6,561,190), the ResMed ULTRA MIRAGE™ mask (disclosed in U.S. Pat. No. 6,691,707), the ResMed VISTA™ mask (disclosed in US Published Patent application 2003/0196657), the ResMed ACTIVA™ mask that includes an elbow with a vent (disclosed in International Patent Application PCT/AU03/01162 published as WO 2004/022147) and the ResMed MERIDIAN™ disposable nasal mask that includes an elbow incorporating a vent (disclosed in International Patent Application PCT/AU2004/000563). The contents of all of these patents and patent applications are incorporated herein by reference in their entireties.

Various quiet vents are known that provide noise levels generally in the range of 25 dBA or less which makes the vent noise difficult to distinguish from transmitted flow generator noise or general background noise. Examples of quiet vents are disclosed in U.S. Pat. No. 6,581,594 and the Weinmann sintered vent. At least the sintered vent is believed to suffer from poor manufacturability, durability, blockage, humidification, sterility/bacterial growth, and/or cleanability.

There is a long felt and continuing need for quiet gas vents for masks and conduits, that are relatively inexpensive, simple in their construction and easy to maintain. Reducing the noise of gas being exhausted from a mask or conduit can significantly improve the user friendliness of the CPAP treatment. Providing a simple and easy to use low-noise vent can reduce the cost of CPAP treatments and thereby assist in making the treatment more affordable to patients suffering from SDB.

SUMMARY OF THE INVENTION

One aspect of the invention is to provide a vent assembly for quiet washout of exhaled gas, which may be accomplished, e.g., using one or more surface characteristics, such as surface treatment, e.g., roughening, and/or surface contouring, e.g., scalloped portions that may be provided to one or more walls of one or more slotted vent apertures. The aperture may take the form of a single arcuate or semi-circular slot having opposed walls that may subtly converge towards and/or diverge from one another in the direction of flow. The slot may take the form of a linear slot and the walls may be parallel to or non-tapering relative to one another in other embodiments.

In another aspect of the invention, a mask includes a vent assembly having an aperture including one or more of the following features: a curvilinear shape, a slot, converging and/or diverging side walls, surface roughness, scalloping/crenations, a rounded or bell-shaped inlet, a development length and/or exit (or minimal) width designed to develop appropriate gas washout, and/or material properties (e.g., density, thickness) to promote quiet exiting of gas.

A particularly preferred embodiment includes a mask with a vent assembly including an aperture including one or more of the following features: a curvilinear shape, a rounded or bell-shaped inlet and/or a development length and/or exit (or minimal) width designed to develop appropriate gas washout.

The invention may be embodied as a washout vent for a mask for use with a system for supplying breathable gas pressurized above atmospheric pressure to an airway of a mammal, the washout vent comprising a vent orifice adapted for gas washout, wherein said orifice at least partially defines or completes a conic section, e.g., a circle, ellipse, parabola, hyperbola, etc. In one preferred example, the orifice completes about 220°-300°, and preferably 270°, of a circle or an ellipse.

The vent assembly may comprise a single orifice having a shape of a horse-shoe, ellipse, spiral, curved, straight crescent(s), semi-circle, curvilinear slot portions thereof, or any combination of the above. The orifice may be a plurality of orifices arranged on the mask or a removable vent assembly insert. Further, the vent comprises a channel between the orifice and the mask shell, wherein the channel has a depth at least as thick as a thickness of the mask and preferably at least four times larger than a width of the orifice. The sidewalls of the channel may converge towards each other and may have a coarse or roughened surface treatment and/or a scalloped surface, to reduce the noise of the washout gas exhausting through the orifice.

In another embodiment, the invention may comprise a vent assembly for washout of gas from a mask used with a system for supplying breathable gas pressurized above atmospheric pressure to a human or animal patient, said vent assembly comprising: an orifice in fluid communication with an interior of the mask, and a solid section at least partially surrounded by the orifice. The vent assembly may be an insert formed from an elastomeric material that is substantially softer and more flexible than the hard plastic mask shell, and said insert is selectively and repeatably attachable to and detachable from the mask. The vent assembly may be substantially crescent-shaped and includes one or more orifices therethrough. The orifice may have a conic shape e.g., selected from a group consisting of a horse-shoe, crescent, a 270 degree semi-circle and a curvilinear slot, etc. Further, the vent assembly comprises a channel extending between the orifice and the interior of the mask, and the channel comprises sidewalls surface treatments, such as a coarse or roughened surface, and the sidewalls may be scalloped.

Another aspect of the invention relates to a washout vent for a mask for use with a system for supplying breathable gas pressurized above atmospheric pressure to an airway of a mammal. The washout vent includes a vent orifice adapted for gas washout. The orifice includes opposed edges or side walls. A channel is provided between an orifice exit and an interior surface of the mask. The orifice has a curved configuration including a diameter in the range of 4-20 mm extending through an arc in the range of 130-150 degrees. The channel includes a width in the range of 0.5-1.0 mm, a depth in the range of 2.5-3.5 mm, an inlet radius in the range of 1-2 mm, and a draft angle in the range of 3-7 mm.

Yet another aspect of the invention relates to a mask assembly including a mask frame and two washout vents provided to the mask frame. Each of the vents includes an elongated, curved vent orifice adapted for gas washout.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 23-25 illustrate still another embodiment according to the present invention.

FIGS. 28-34 illustrate additional vent orifices having shapes according to embodiments of the present invention.

FIG. 35 is a front plan view of a mask frame including washout vents according to an embodiment of the present invention.

FIG. 36 is a cross-sectional view of a vent a taken along line 36-36 of FIG. 35 and showing dimensions of an embodiment.

FIG. 37 is an enlarged plan view of a vent taken from FIG. 35 and showing dimensions of an embodiment.

DETAILED DESCRIPTION OF ILLUSTRATED EMBODIMENTS

1. First Embodiment of Gas Washout Vent

Figure 1:
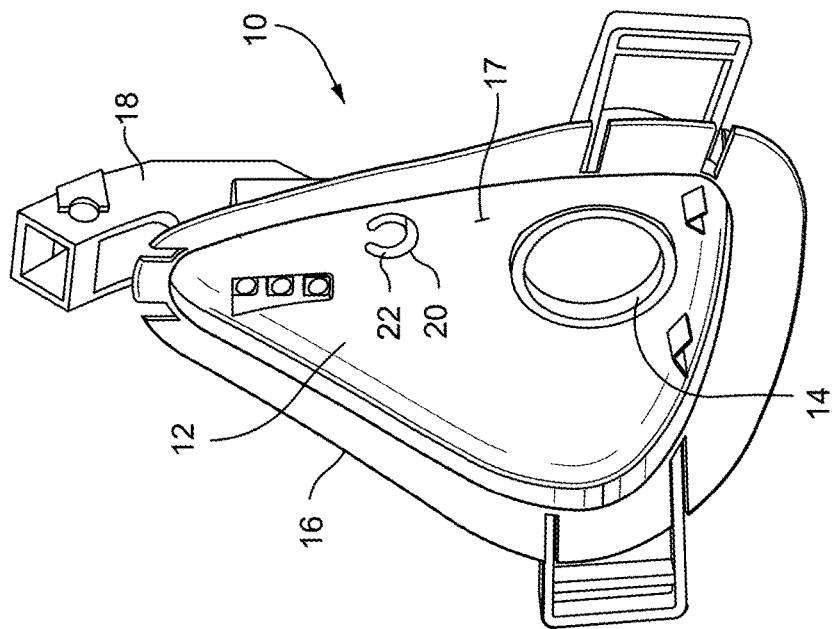
FIGS. 1 and 2 show respectively a front isometric view and rear isometric view of a mask frame incorporating a vent in accordance with a first embodiment of the invention.
Figure 2:
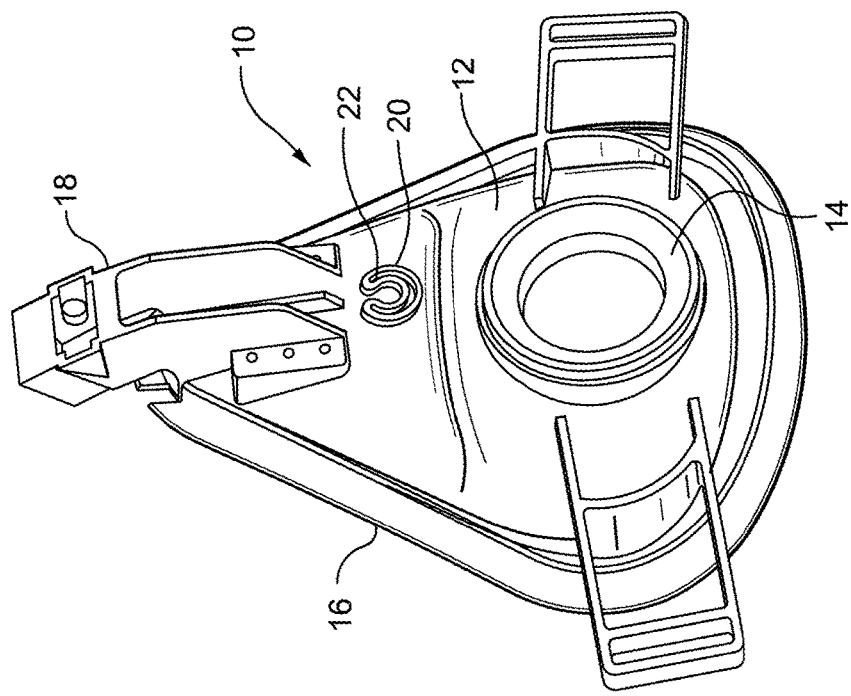

FIGS. 1 and 2 show a mask frame 10 for use with a system for supplying breathable gas pressurized above atmospheric pressure to an airway(s) of a human or other mammal, e.g., a CPAP or other non-invasive positive pressure delivery system. The mask frame includes a rigid plastic shell 12 having an air inlet tube aperture 14 for connection to a supply conduit to communicate breathable gas from a flow generator (not shown) to the airways of the mask wearer. The mask shell 12 includes a rim 16 which supports a flexible sealing membrane (not shown) that provides a gas tight seal between the face of the patient and the interior volume 17 of the shell 12. The shell 12 includes a support 18 for connecting the mask 10 to a forehead support (not shown) which includes, e.g., a T-Bar having slotted connectors for receiving headgear straps that retain the mask over the nose and/or mouth while the patient sleeps. The mask frame may be molded from a generally rigid material such as polycarbonate.

A vent 20 on the mask includes an orifice 22 for gas washout. The orifice is partly defined by channel 26 (FIG. 6) that provides a flow passage from the interior 17 of the mask to the atmosphere. The orifice may in plan view have a conic shape, e.g., opposed walls or edges defining the orifice may be formed in any shape that can be defined by a complete or partial cross-section taken through a cone or a partial conic section. For example, the orifice may be in the form of a circle, hyperbola, ellipse, parabola, semi-circle, or portions thereof. In addition, the opposed walls or edges of the orifice may define other shapes, such as a "C", horse-shoe, crescent, a pair of opposing crescents, sinusoidal curves, a series of convex and concave segments, spiral, portions or sections thereof, or other curvilinear or even linear shapes.

In another sense, the orifice is provided on a solid section 32 of the mask that forms a peninsula that is partially surrounded by the orifice. The solid section may be a plate with a bridge to the mask. The solid section may be in a plane common to the mask and recessed with respect to the orifice or the solid section may be recessed relative to the remainder of the mask such that the vent aperture is flush with the outside of the mask.

A common characteristic of one embodiment of the curvilinear or linear orifice is that the orifice has a length (L—FIG. 3) substantially greater than its characteristic width (W). For example, the length (L) may be at least five (5) times the width (W) of the orifice, and the length may be preferably 10 to 20 times the width. This ratio may in certain applications be less than five and greater than 20. If the orifice is a plurality of circle segments (or other arrangement of segments) the combined length (L) of the segments is substantially greater than their average width. Further, the area of the orifice, e.g., length times width (depending on the shape of the orifice), is preferably about 15 mm² and may be in a range of, for example, 5 mm² to 25 mm². The smallest cross-sectional area of the orifice, which may occur anywhere along the length of the channel or orifice, defines the resistance of the vent.

Figure 5:
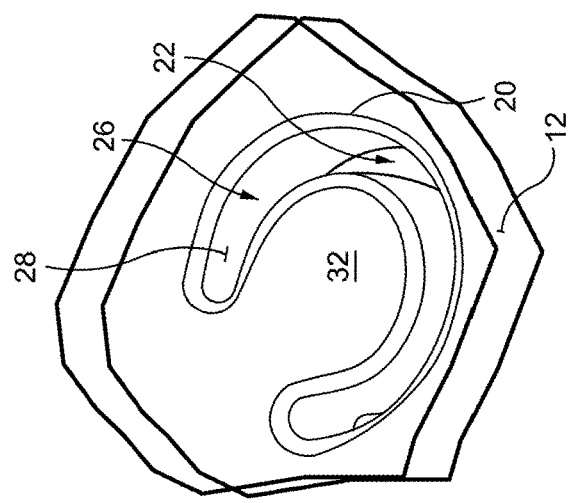
FIGS. 3, 4 and 5 show respectively a front plan view (viewed from the mask exterior), a front isometric view and a rear isometric view (viewed from mask interior) of the vent shown in FIGS. 1 and 2.
Figure 4:
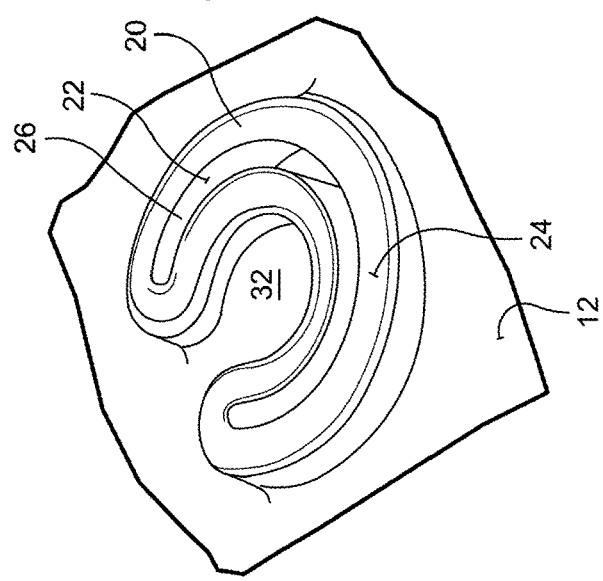
Figure 3:
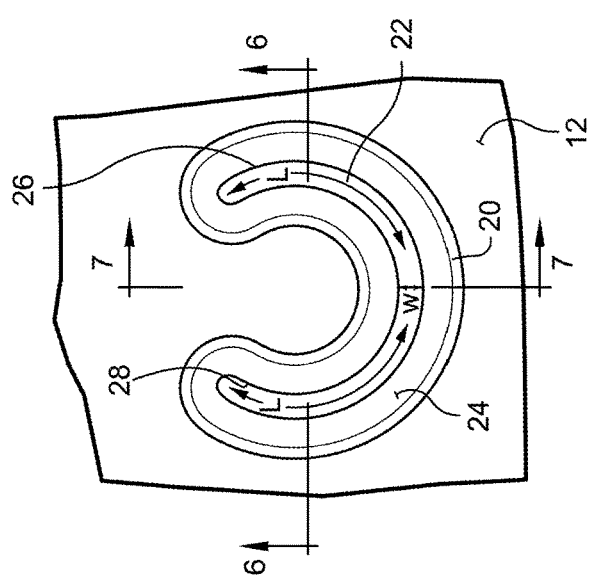

As shown in FIGS. 3, 4 and 5, the orifice 22 may be formed at the apex of a raised ridge 24 extending outward from the mask shell or at the bottom of a groove formed in the shell. In the embodiment shown in FIGS. 1 to 5, the ridge 24 in plan view is a three-quarters (¾) section of a circle, i.e., it accommodates for and matches the shape of the orifice.

It is thought that an orifice of the configuration shown in FIGS. 3-5 helps reduce noise, at least in part, because the jetted air encounters, on exit, air that is not necessarily stagnant, but is moving somewhat due to neighboring sections of the orifice that promote the movement of such jetted air in the exit direction. Stated differently, the curved nature of the slot, especially one that "folds over" on itself, in the form of a curvilinear section, helps minimize the difference in velocity between the jetted air and the surrounding environmental air.

The ridge and/or its orifice may be segmented to form, for example, an array of circle segments or a pair of opposite crescent ridges. The orifice, when in the form of a semi-circular shape, defines a peninsula 32 that connects to and is formed as part of the mask. The ridge or groove may have a shape similar but wider than the shape of the orifice.

The diameter (D) (see FIG. 6) of the circle formed by the orifice is preferably about 6-8 mm, preferably about 6 mm, and may be in a range of 4 mm to 20 mm. The diameter (D) of the semi-circular orifice may be determined based on the desired surface area, e.g., 15 mm², of the orifice. Further, the diameter (D) may vary beyond the suggested 4 mm to 20 mm range depending on the application.

The inner surfaces 28 of the orifice 22 define, or are defined by, a channel 26 extending from the interior 17 of the mask shell to the exit of the orifice 22. The channel 26 may be curvilinear, e.g., horse-shoe shaped, and have a shape similar to the exit of the orifice. In the illustrated embodiment, a gap (W) of the orifice 26 generally narrows (converges) from the mask interior surface to the exit of the orifice. However, the orifice may also diverge in the direction of flow, or the orifice may have a complex shape such that it diverges in one section, and converges in another section of the orifice, in the direction of the flow of gas. In the illustrated embodiment, the gap of the orifice is open to the interior 17 of the mask shell. The gap between inside surfaces 28 of the channel walls may be approximately 0.5 mm to 1.0 mm, and preferably 0.75 mm at its narrowest width. The slope of each inner surface may be a draft angle (DA) of 5° from an axis extending through the channel. While a draft angle of 5° is preferred, other draft angles are possible such as angles ranging from 3 to 7 degrees.

The channel 26 may have a depth (DD) approximately four times the narrowest width of the channel gap (W). The channel depth (DD) is a distance from an inside surface of the mask shell to the exit of the orifice. In a preferred form, the channel depth is 3 mm and the gap (W) is 0.75 mm. The channel depth is generally greater than the thickness (T) of the mask shell, such that the vent and orifice protrude from the surface of the shell. The mask may have a thickness of 1.0 mm. The ratio of the channel depth (DD) to the width (W) of the orifice is preferably 4.0 (e.g., 3.0 mm/0.75 mm), and may be in a range of 2 to 100.

2. Second Embodiment of Gas Washout Vent

FIGS. 8 to 11 show a channel 26 in which the sidewalls 28 have surfaces shaped and/or treated to increase turbulence of air exhausting from the channel and into the atmosphere. This has the effect of quickly mixing the vented air with the air from atmosphere, to thereby rapidly reduce the velocity of vented air—which is thought to reduce noise. At least a portion of the interior surfaces 28 of the channel may have a shaped surface, for example, being scalloped with crenated edges, and/or a treated surface, e.g., a coarse surface treatment such as a roughened or scaled surface. One example of roughening may be in the order of 100-200 microns. The surface treatment may be applied to the inner surfaces of the channel near the orifice. Scaled refers to a surface treatment that appears similar to the scales on a fish, such as a shark.

Figure 7:
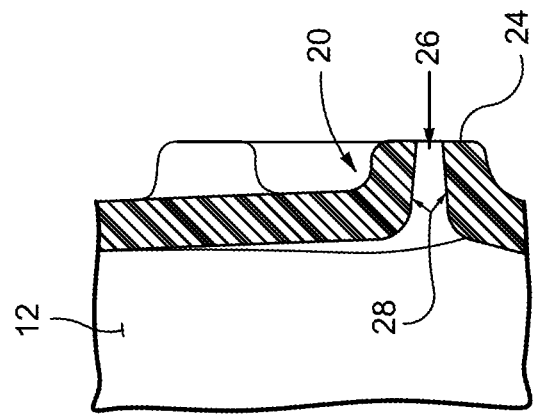
FIGS. 6 and 7 are cross-sectional views of the vent taken along lines 6-6 and 7-7 respectively of FIG. 3.
Figure 6:
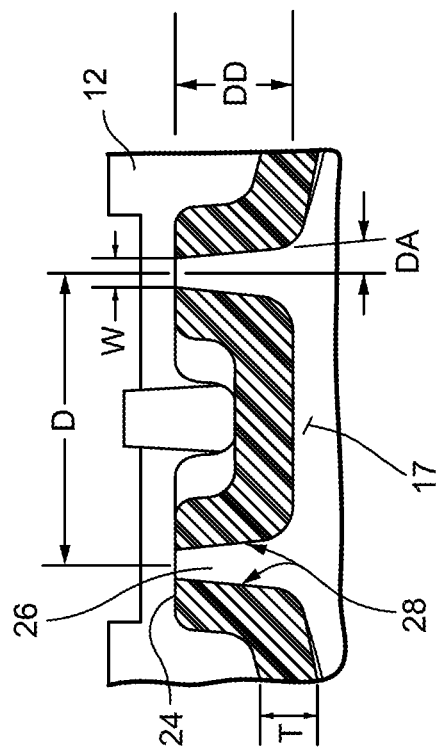
Figure 10:
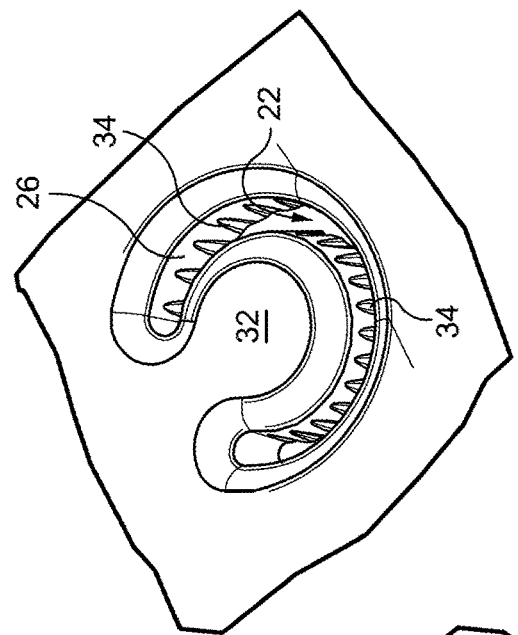
FIGS. 8 to 10 show respectively a front plan view (viewed from mask exterior), a front isometric view and a rear isometric view (viewed from mask interior) of a second embodiment of the vent.
Figure 9:
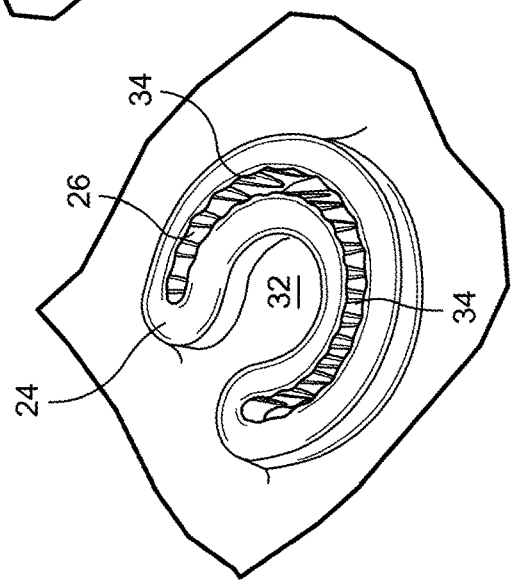
Figure 8:
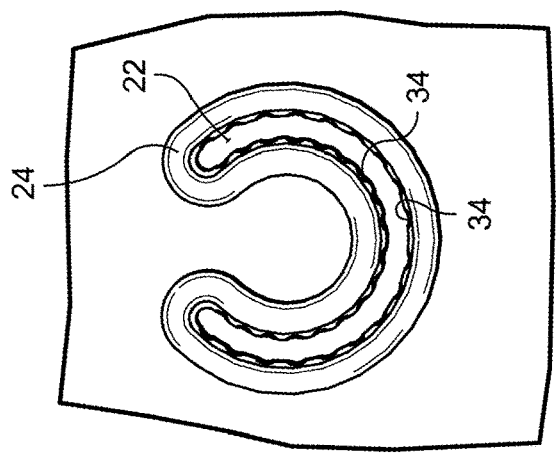
Figure 12:
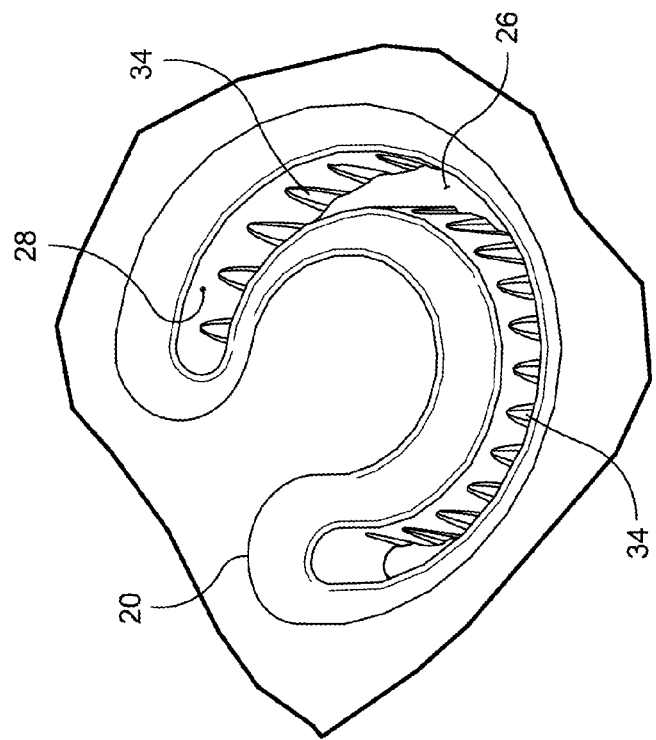
FIGS. 11 and 12 are rear plan and rear isometric enlarged views showing a scalloped surface treatment and crenated outlet edge of the second embodiment of the vent.

In one embodiment, the surface contouring or shaping may include a series of scalloped grooves 34, e.g., 10-30 grooves, and preferably about 18 grooves in the illustrated example, in each of the interior surfaces of the channel as are shown in FIGS. 8 to 12. While the grooves 34 are illustrated to have the same dimensions, the size of the grooves could alternate between larger grooves and smaller grooves, or each of the grooves could have a different size. Further, at the channel inlet, the side walls may be smooth and not scalloped. As shown in FIGS. 6, 7 and 12, the base of the interior walls 28 is well rounded or bell-shaped to facilitate passage of air. Smooth inner surfaces 28 may extend at least down to one-half the depth of the channel.

Conceptually, the shape of the scalloped grooves may be formed by cutting with cylindrical drill bits that have a diameter wider than the orifice (W) and narrower than the widest portion of the channel. Drilling the sloped channel sidewalls with cylindrical drill bits forms scalloped grooves beginning at the narrow outlet of the channel and extending inward along a portion of the walls. Drilling the grooves also yields parabolic edges along the inner walls of the vent. Alternatively, and preferably, the scalloped grooves may be formed during molding by vent molds that include scalloped ridges on the walls of the mold corresponding to the vent channel. It should be noted that scalloping can be provided on side walls even if they do not taper, conceptually by using a conical drill bit and drilling from the exit of the orifice inward.

Figure 11A:
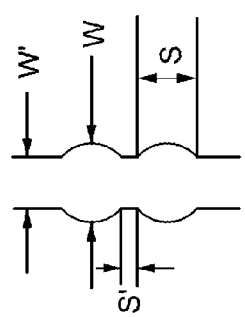
FIG. 11A is a schematic view showing exemplary dimensions and geometry of a vent orifice according to an embodiment of the present invention.
Figure 11:
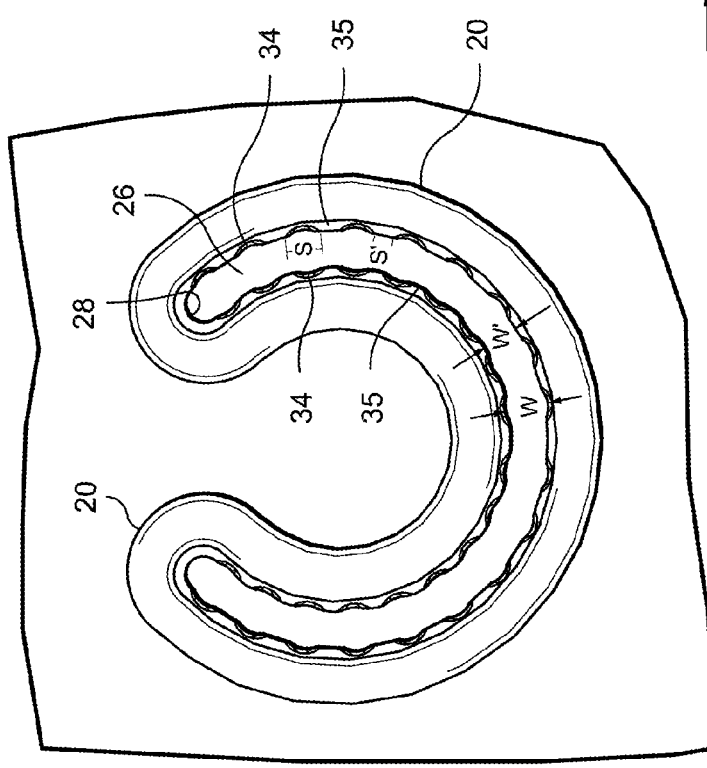

The outlet edges of the channel, such as surrounding the orifice, may be crenated. The outlet edge 35 of the channel may be a sequence of relatively straight segments (S') and interleaving crenated segments (S), e.g., elliptical or rounded segments. The alternating straight and crenated segments of the channel edge promote mixing of the jet stream exiting the vent with stagnant air just downstream of the channel outlet. While the edge segments (S' and S) are shown as being relatively uniform, the segments may vary in length and depth along the edge of the channel. In addition, the width (W') of the channel is smaller than the width (W) of the channel for the scalloped portions to be formed. FIG. 11A is a schematic view showing the relative positions of these dimensions.

3. Third Embodiment of Gas Washout Vent

Figure 13:
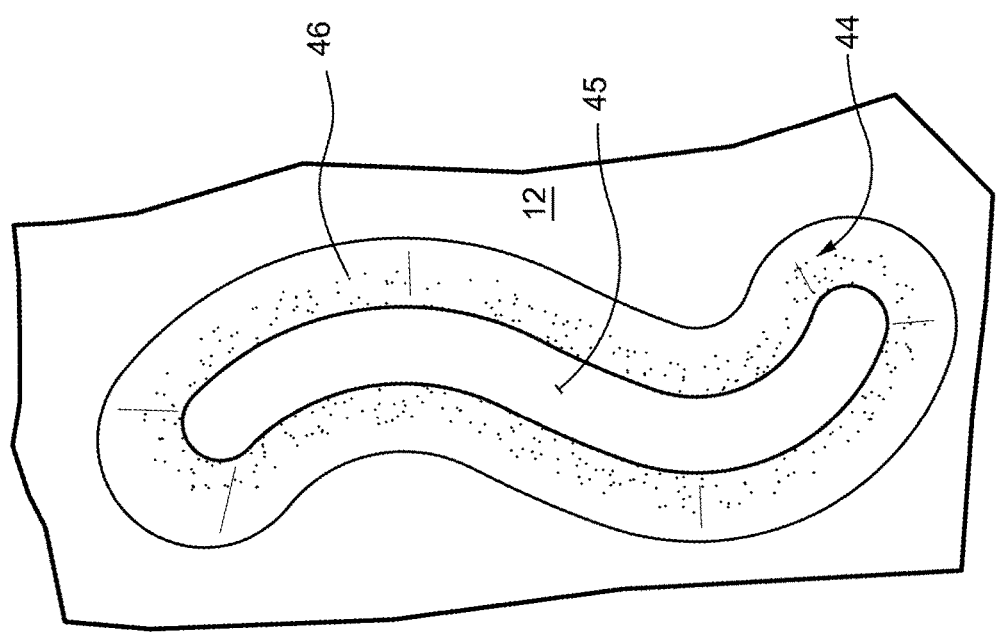

FIG. 13 is a front plan view of another embodiment of a vent orifice 45 having channel sidewalls 44 that have a coarse surface treatment 46 at least near the edge of the channel at the orifice preferably at the exit edge. The coarse surface is believed to increase the turbulence of air flowing along the sidewalls of the channel. The orifice 45 and the associated channel (which may be a ridge extending outward from a mask shell 12 or a groove extending into the shell) has a curvilinear shape that has a serpentine sequence of convex and concave curve segments. The coarse surface treatment may be separate from or combined with the scalloped grooves on the channel sidewalls. The interior walls 44 of the channel may be made coarse 46 by, for example, sandblasting the portion of the mold corresponding to the vent channel.

To mold the vent (either as a separate vent or vent integral with the mask) a mold is first formed of the vent, wherein the mold comprises a ridge corresponding to a channel and orifice of the assembly. The geometry of the mold may be cut to include scalloping features, and the surface of the mold may be treated, e.g., via sand blasting, to produce the desired level of surface roughness on the interior surfaces of the vent. The surface treatment or contouring is preferably applied to the mold sidewalls on opposites sides of the mold section corresponding to the vent channel and particularly to the exit edge of the vent (orifice). A plastic material (e.g., polycarbonate) is injected into the mold to form a molded vent assembly having a channel that possesses the scalloped and/or surface roughness of the mold.

4. Fourth Embodiment of Gas Washout Vent

Figure 14:
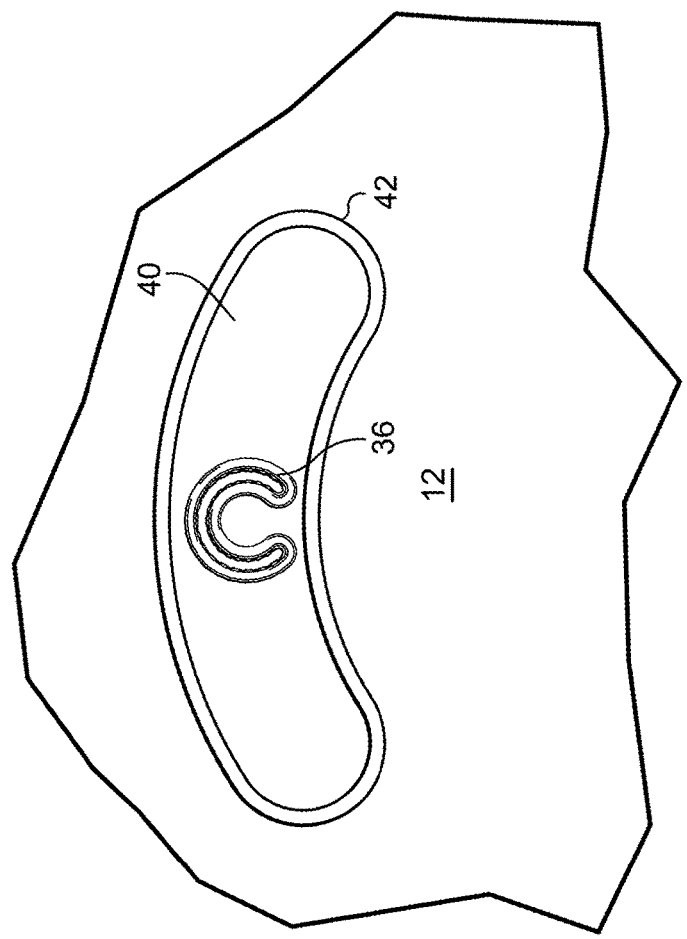
FIGS. 13 and 14 are front plan views of alternative embodiments of the vent.

FIG. 14 is a plan view of alternative orifice 36 and a removable elastomeric insert 40 that fits into an aperture 42 in a mask shell. Vent inserts are known and disclosed in, for example, U.S. Pat. Nos. 6,561,190 and 6,561,191 and US Patent Application Publication 2003/0079751, each incorporated by reference in its entirety. Whereas vent inserts typically have had an array of small circular orifices, the orifice 36 in FIG. 14 is an extended curvilinear slot. Alternatively, or in addition, the orifice 36 may include a channel as described above with a predetermined draft angle, roughening, and/or one or more scalloped portions. The vent insert in FIG. 14 may be identical in its outside shape to an existing insert and may fit into existing mask shells. The curvilinear orifice in the replaceable vent 40 allows for curvilinear slots (such as those shown in this disclosure) to be used on existing mask assemblies. The insert 42 may be formed of a flexible polymer, e.g., Santoprene™. The inserts 42 are removable for replacement and cleaning.

5. Gas Washout Vent on Alternative Mask

Figure 15:
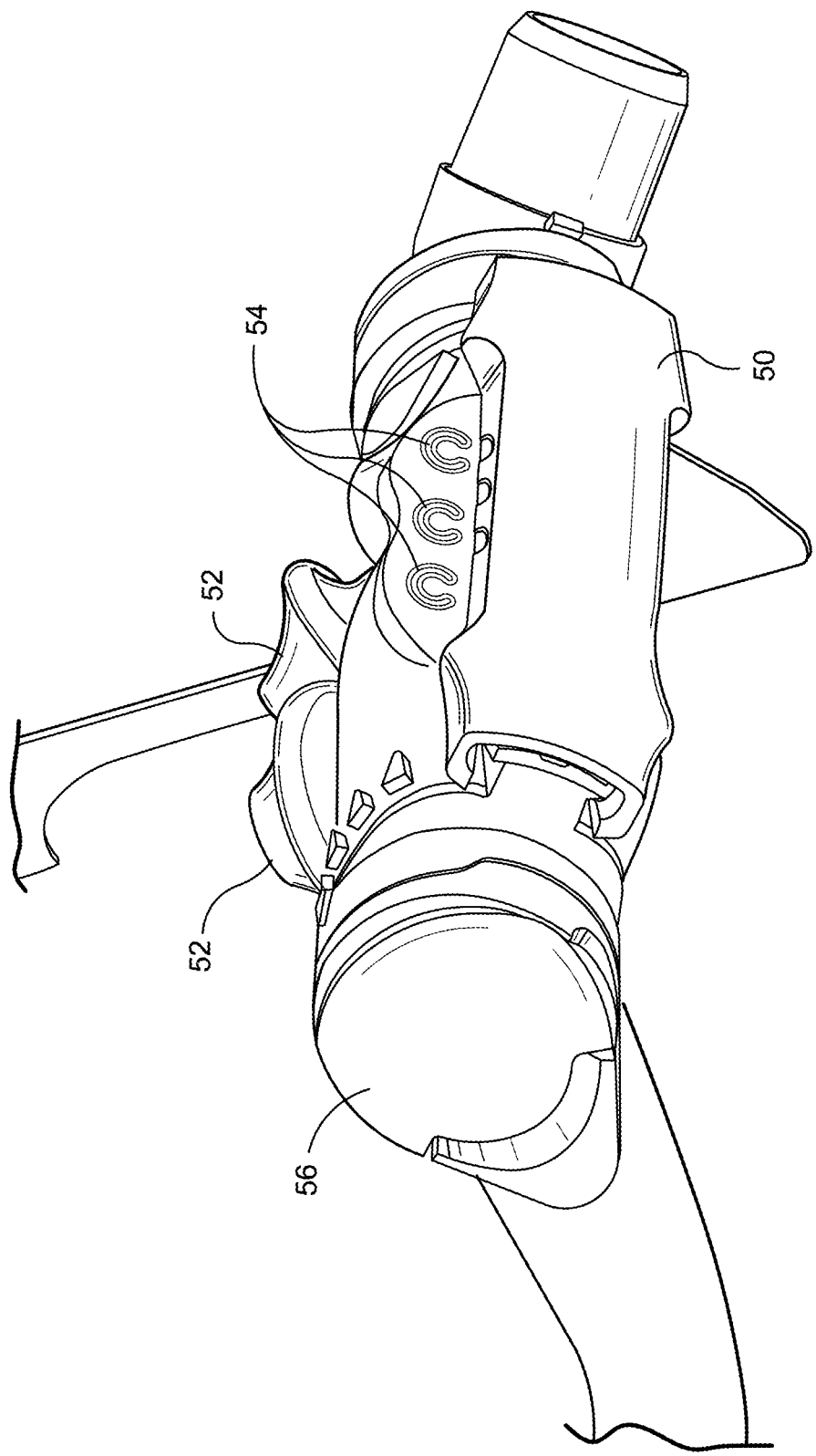
FIG. 15 is a front view of a vent on an alternative mask.

FIG. 15 is a perspective view of a mask 50 that includes nozzles 52 that interface with the nares of the patient. Similar masks are disclosed in, for example, FIGS. 117 and 130 of US Patent Application Publication No. 2004/0226566, which publication is incorporated by reference in its entirety. Whereas washout vents conventionally have been an array of circular openings, the present mask includes one or more curvilinear vents 54 including one or more of the features described above in relation to FIGS. 3-12, e.g., a slot with converging walls, optionally provided with surface contouring or surface treatment, e.g., scalloped portions and/or roughening. The illustrated vent assembly has one or more elongated orifices that are believed to operate quieter than do the conventional circular vent orifices.

Figure 16:
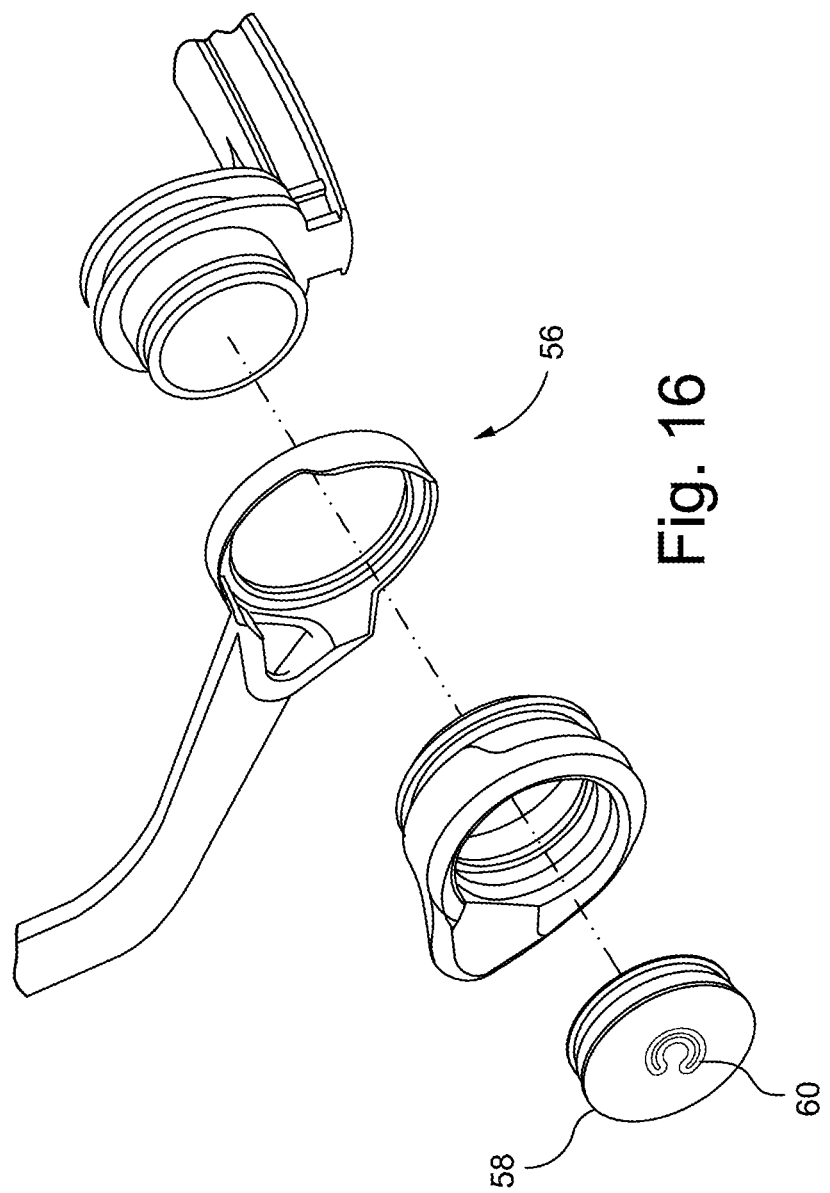
FIG. 16 is a exploded view of an alternative end cap for the mask shown in FIG. 15.

FIG. 16 is a partial exploded view of a yoke, frame, sealing ring and end cap assembly 56 for the mask shown in FIG. 15. The end cap 58 shown in FIG. 16 has a curvilinear washout vent 60. Positioning a single large orifice vent on the end cap avoids a need for a plurality of vents on another portion of the mask such as the cushion.

6. Swivel Elbow With Gas Washout Vent

Figure 17:
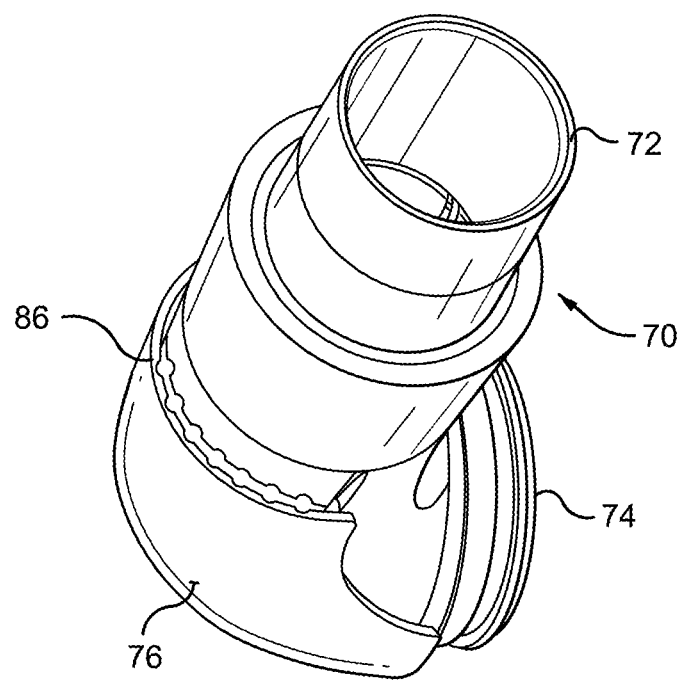
FIG. 17 is a front isometric view of a swivel elbow with a vent.
Figure 18:
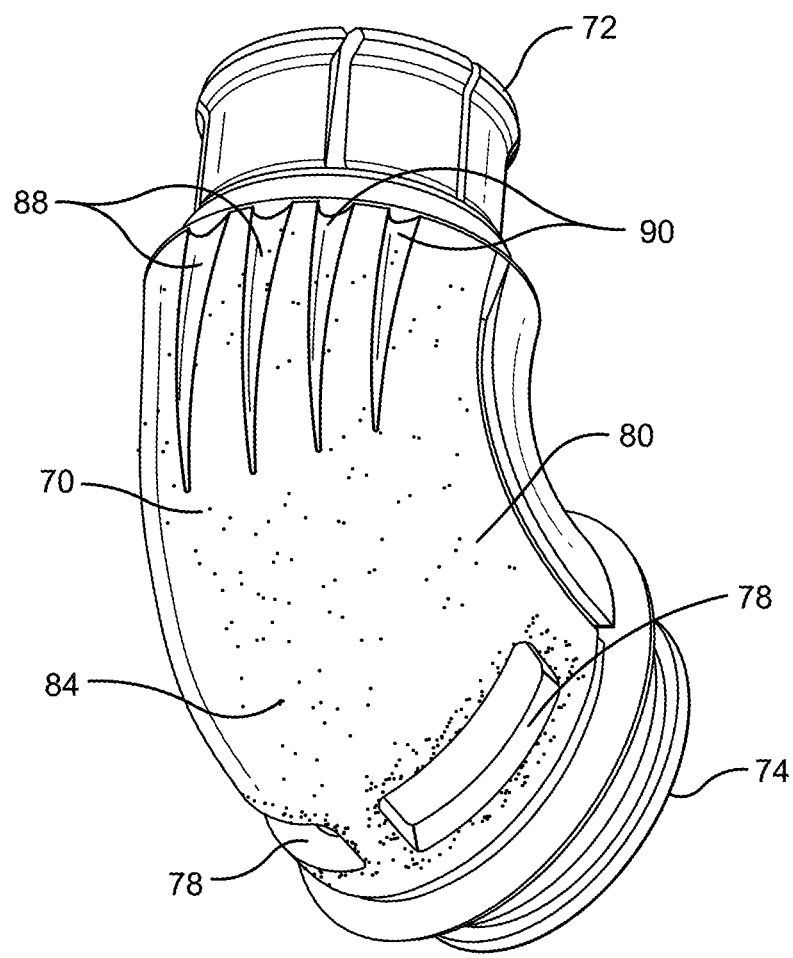
FIG. 18 is a front isometric view of the gas conduit shown in FIG. 17 without a vent shield.
Figure 19:
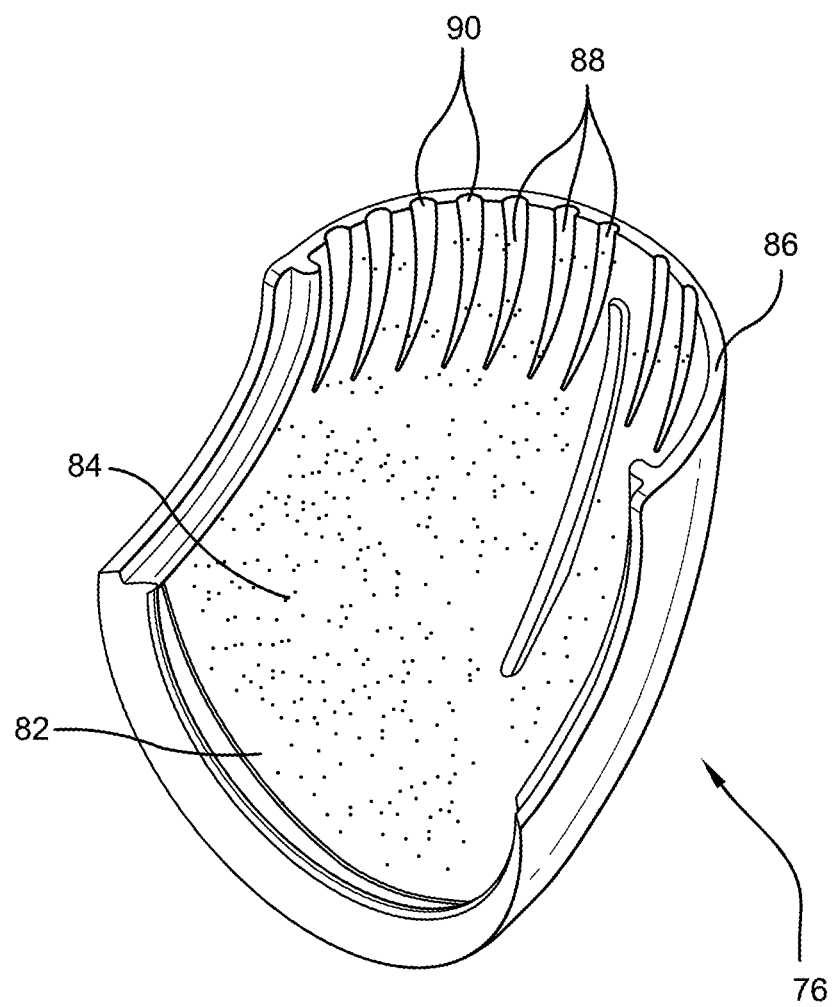
FIG. 19 is a rear isometric view of the vent shield for the conduit shown in FIG. 17.
Figure 20:
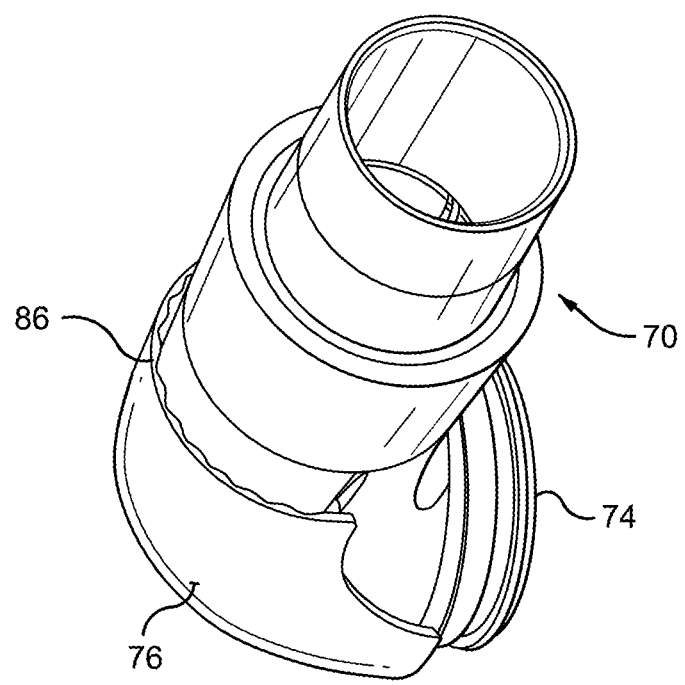
FIGS. 20 and 21 illustrate a vent assembly according to yet another embodiment of the present invention.
Figure 21:
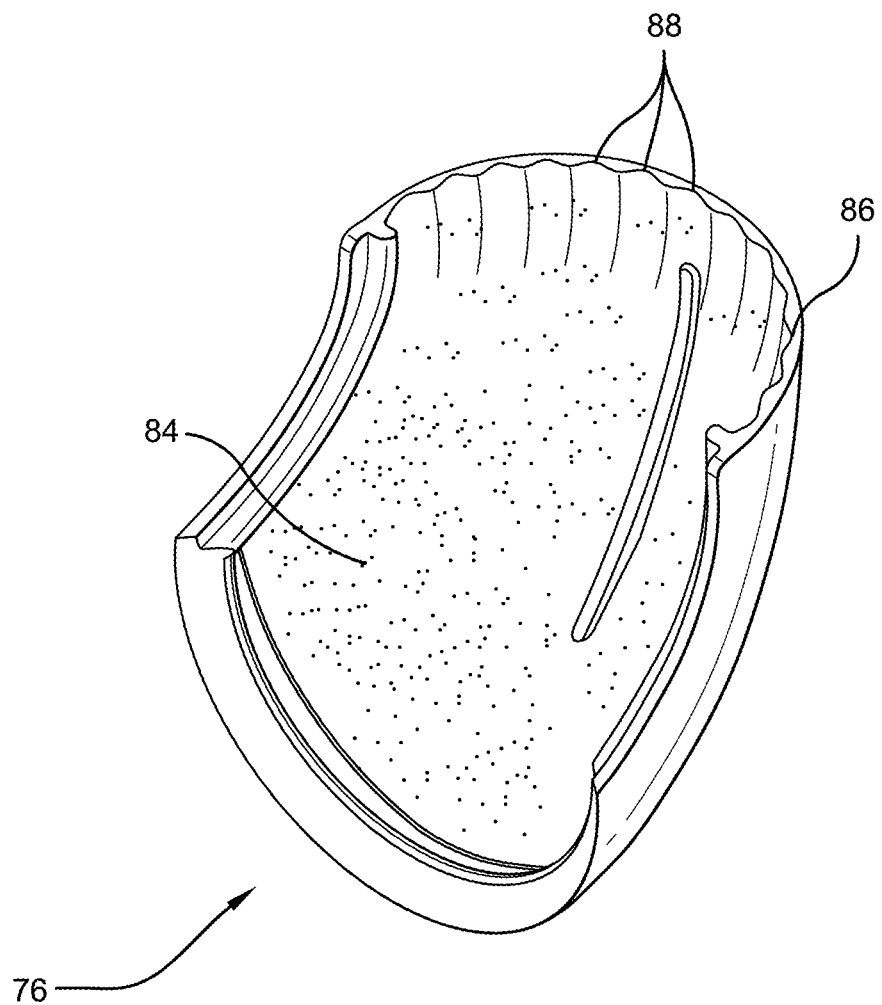

FIGS. 17, 18 and 19 are views of an air inlet conduit 70 that has an air inlet 72 and an air outlet 74, similar to that shown in U.S. Pat. No. 6,691,707, the entirety of which is incorporated by reference. A hose (not shown) fits to the inlet to provide pressurized air from a blower or other source of air. The outlet 74 fits to an aperture in the mask, such as aperture 14 in the mask shown in FIG. 1. An elbow in the conduit 70 includes a vent shield 76 that covers at least one vent orifice 78 (shown in FIG. 15) which may be a series of curvilinear slot orifices. The orifices exhaust washout gases into a gap between an outer surface 80 of the conduit and an inner surface 82 (FIG. 16) of the shield. A coarse surface treatment 84 may be applied to the inner surface 82 and outer surface 80 in the area corresponding to the gap, especially near the outlet to atmosphere. The gap receives washout gas from the vents 78 and exhaust the gas at an end 86 of the shield. Scalloped grooves 88 may be formed on the surfaces 80, 82, such as near the end 86 of the shield. The grooves form crenated edges 90 at the outlet of the gap. These edges 90 promote mixing of the washout gas exhausting from the gap with stagnant atmospheric air, which is thought to rapidly decrease the velocity difference (shear rate) between the atmosphere, reducing exhausted gas and the attendant noise thereof.

7. Mask Assembly with Vent Assembly

Figure 22:
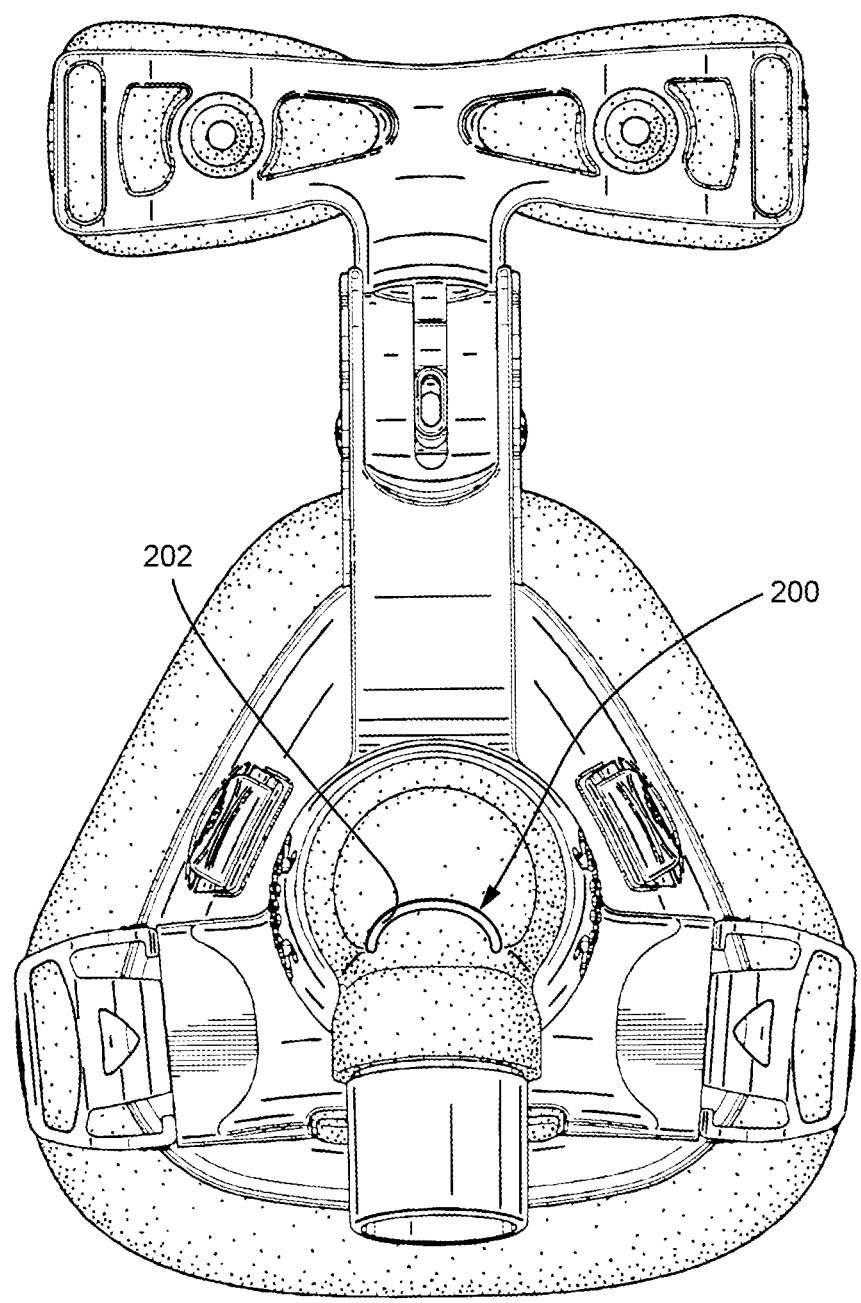
FIG. 22 illustrates a vent assembly according to still another embodiment of the present invention.

FIG. 22 illustrates another embodiment of the invention showing a mask assembly adapted to include a vent assembly 200 having one or more surface treatments (scalloping/roughening) that may be applied to a single curvilinear aperture 202 provided on the vent cover. More details of this mask assembly are disclosed in U.S. patent application Ser. No. 10/655,621 filed Sep. 5, 2003, incorporated herein by reference in its entirety.

8. Alternative Mask Assembly with Vent Assembly

FIGS. 23-25 illustrate a mask assembly including a vent assembly 300 according to yet another embodiment of the present invention. Vent assembly 300 is part of a ResMed mask more fully described in U.S. Pat. No. 6,112,746, incorporated herein by reference in its entirety. The mask assembly may include one or more attributes of the vent assembly described in relation to FIGS. 3-12.

9. Alternative Mask Assembly with Vent Assembly

Figure 26:
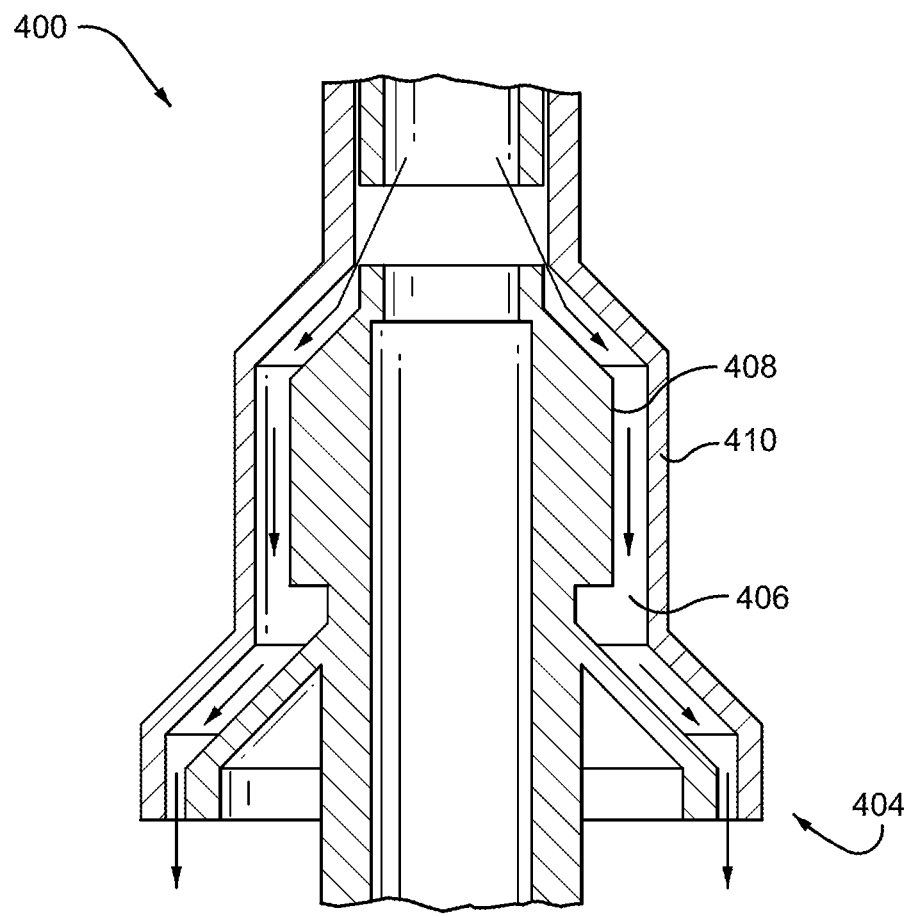
FIGS. 26 and 27 illustrate yet another vent assembly according to an embodiment of the present invention.
Figure 27:
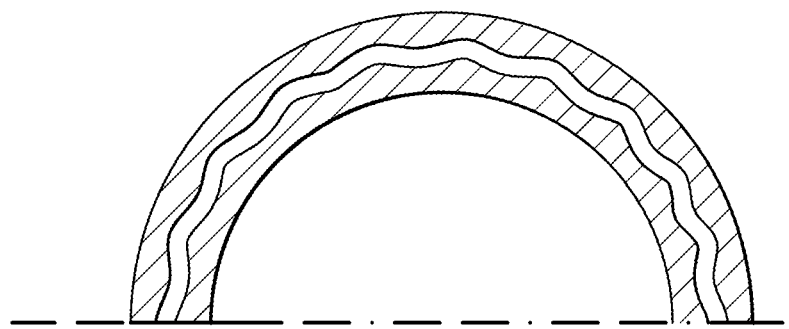
Figure 40:
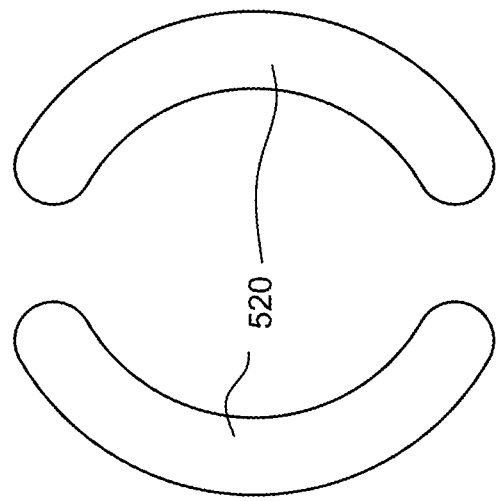
FIGS. 38-44 illustrate alternative embodiments for orienting two vents on a mask frame.
Figure 39:
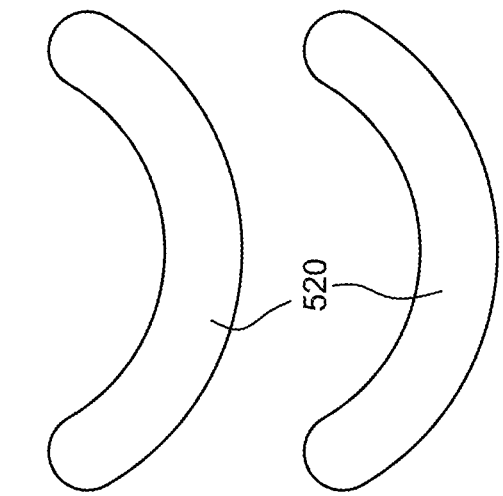
Figure 38:
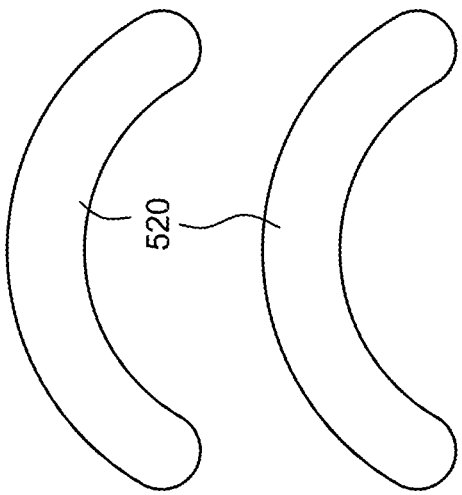
Figure 42:
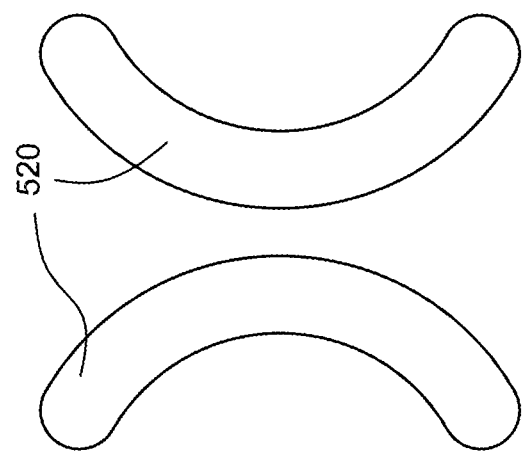
Figure 41:
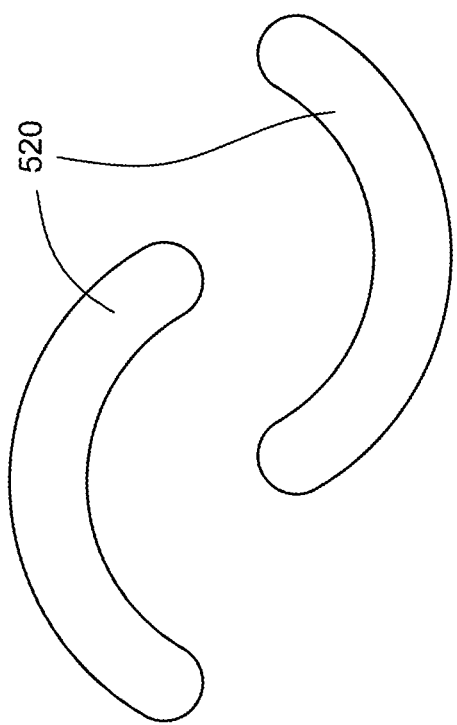
Figure 44:
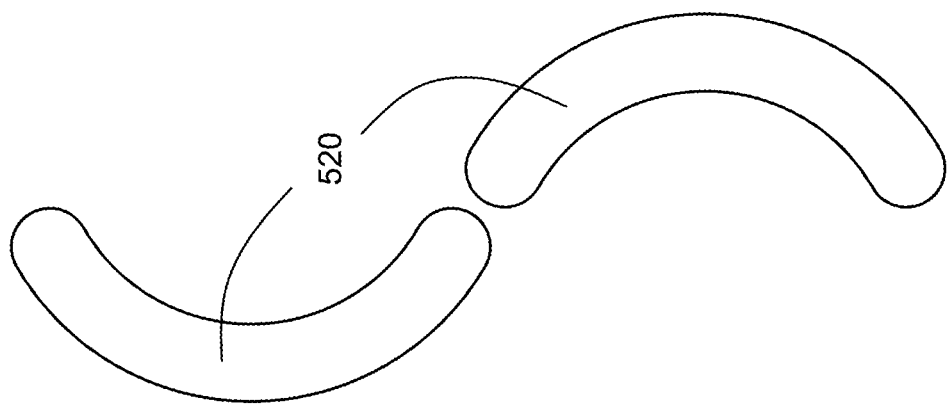
Figure 43:
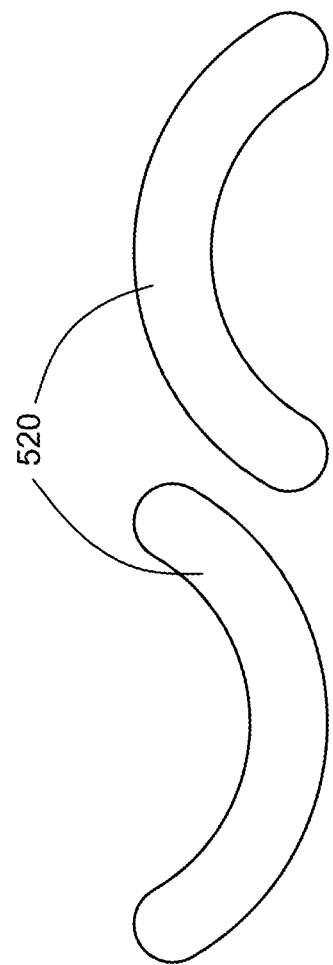

FIGS. 26 and 27 illustrate a portion of a mask assembly 400 as described in EP 0 985 430 A2, incorporated herein by reference in its entirety. The mask assembly includes a vent assembly 404 to exhaust exhaled gas to atmosphere, e.g., via path 406 defined by an interior wall 408 and an exterior wall 410. Each wall 408, 410 may include one or more surface treatments, e.g., scalloping and/or roughening, as described above.

10. Vent Orifice Shapes

FIGS. 28-34 illustrate further orifice shapes according to the present invention. In each embodiment, the total open area of the orifice is selected to address adequate gas washout, as described above. FIG. 28 is a ¾ ellipse, as compared to the ¾ circle in FIG. 29. FIG. 30 shows two parts of an ellipse having areas A1 and A2 which combined form a total Area ($A_{TOTAL}$). FIG. 31 shows a generally curvilinear orifice, while FIG. 32 shows a spiral shaped orifice having multiple component radii ranging from R1 to R2. FIG. 33 illustrates an orifice with curved and straight sections (delineated by section lines), while FIG. 34 shows an "S"-shaped orifice having radii R1 and R2 that are equal.

11. Mask Frame with Two Curved Washout Vents

FIGS. 35-37 illustrate a mask frame 510 including two curved washout vents 520 according to an embodiment of the present invention. The vents 520 have a generally similar vent structure to the vents 20 described above in relation to FIGS. 1-7. However, the two vents 520 are oriented on the mask frame 520 in a particular manner. Also, the vents 520 include specific dimensions for an embodiment.

specifically, each vent 520 includes a diameter of 7.7 mm extending through a 142 degree arc (see FIG. 37). This arrangement improves the strength of the vent material when compared to a larger arc. As shown in FIG. 36, each vent 520 also has a width of 0.85 mm, a depth of 3 mm, an inlet radius of 1.5 mm, and a draft angle of 6 degrees. Although specific dimensions of the vents 520 are shown in FIGS. 36 and 37, it is to be understood that these dimensions are merely exemplary and other dimensions are possible depending on application. For example, the diameter may be in the range of 4-20 mm, preferably 6-8 mm, extending through an arc in the range of 130-150 degrees. The width may be in the range of 0.5-1.0 mm, the depth may be in the range of 2.5-3.5 mm, the inlet radius may be in the range of 1-2 mm, and the draft angle may be in the range of 3-7 mm. Also, the vents 520 may include one or more additional features as described above, e.g., surface contouring or surface treatment. Further, the vents 520 may include other orifice shapes such as those described in FIGS. 28-34.

As shown in FIG. 35, two vents 520 are provided to the mask frame 510. As illustrated, the mask frame 510 includes a receiver 562 adapted to receive a forehead support. The two vents 520 are positioned on the mask frame 510 between spaced-apart side walls 564 of the receiver 562. In addition, the two vents 520 are positioned end to end with a small gap therebetween so that they together define a generally reverse-S shape. Further, the two vents 520 are oriented such that a line L extending through a center of each vent 520 is generally perpendicular to a longitudinal axis A of the mask frame 510.

This vent arrangement on the mask frame 510 allows the width of each vent 520 to be thinner than if just one vent were used. Also, the two vents 520 may be quieter than one vent, which may be due to the thinner width of each vent and/or more vent perimeter per open area. In addition, two vents 520 may reduce the lateral space required on the frame 510. However, it is to be understood that any suitable number of vents 520 may be provided to the frame 510, e.g., one vent or more than two vents. Also, the vents 520 may be oriented on the mask frame 510 in other suitable manners.

FIGS. 38-44 illustrate several alternative embodiments for orienting two vents 520 on the mask frame. For example, the two vents 520 may be vertically aligned with both vents curved downwardly (see FIG. 38) or both vents curved upwardly (see FIG. 39). The two vents 520 may be horizontally aligned with the vents curved towards one another (see FIG. 40) or the vents curved away from one another (see FIG. 41). The two vents 520 may be vertically offset with the vents curved towards one another (see FIG. 42). The two vents 520 may be positioned end to end with a small overlap (see FIG. 43). Also, the two vents 520 may be positioned end to end with small gap therebetween so that they together define a generally S shape (see FIG. 44). It is noted that additional vent configurations may be created by mirroring, rotating, and/or scaling the vent geometry, e.g., see FIGS. 28-34.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. For example, while the vent assemblies described above may be used in the field of treating patients with sleep disordered breathing, they may also be beneficial to the field of respirators or ventilators in general, e.g., for use in treatment of other illnesses (e.g., congestive heart failure, diabetes, morbid obesity, stroke, barriatric surgery, etc.), or they may be used in any breathing apparatus for use with patients or non-patients when venting in a quiet cost effective manner is desirable.

What is claimed is:

1. A respiratory mask assembly for use with a system for supplying breathable gas pressurized above atmospheric pressure to an airway of a patient for treatment of sleep disordered breathing, the respiratory mask assembly comprising:

a mask including a shell and a seal,
wherein the mask forms an interior pressurizable to a therapeutic pressure above atmospheric pressure,
wherein the shell includes an aperture structured to receive a flow of air at the therapeutic pressure for breathing by the patient,
wherein the seal is constructed and arranged to form a seal with a patient's nose and/or mouth; and
headgear structured and arranged to retain the mask over the patient's nose and/or mouth;
wherein the mask further comprises a washout vent, the washout vent comprising:
a solid mask section; and
a vent orifice extending through a thickness of the solid mask section and adapted for gas washout, wherein said vent orifice includes opposed side walls providing a flow passage that allows gas to flow along the opposed side walls from the interior of the mask to atmosphere in use, and the opposed side walls defining at least a portion of a conic section having a length greater than its width, wherein the vent orifice includes an orifice inlet at the interior of the mask and an orifice exit open to atmosphere, and the opposed side walls converge along their entire length from the orifice inlet to the orifice exit to reduce noise of gas washout.

2. The respiratory mask assembly as in claim 1, wherein the vent orifice defines a solid section of the washout vent in the form of a peninsula.

3. The respiratory mask assembly as in claim 1, wherein the vent orifice comprises a semi-circular slot.

4. The respiratory mask assembly as in claim 1, wherein the conic section defines a hyperbola, parabola, ellipse, circle, any portion of a hyperbola, parabola, ellipse, circle, or any combination of a hyperbola, parabola, ellipse, circle.

5. The respiratory mask assembly as in claim 1, wherein the vent orifice is at an apex of a ridge on the mask.

6. The respiratory mask assembly as in claim 5, wherein the orifice exit is in a plane offset from the mask.

7. The respiratory mask assembly as in claim 5, wherein the ridge is curvilinear in length.

8. The respiratory mask assembly as in claim 1, wherein the orifice exit is in a plane common to the mask.

9. The respiratory mask assembly as in claim 1, wherein the washout vent is provided as an insert attachable to the mask.

10. The respiratory mask assembly as in claim 1, wherein the vent orifice is crescent-shaped.

11. The respiratory mask assembly as in claim 1, wherein the vent orifice is one of a plurality of orifices through the mask.

12. The respiratory mask assembly as in claim 1, wherein the vent orifice has a horse-shoe shape.

13. The respiratory mask assembly as in claim 1, wherein the vent orifice comprises convex and concave segments.

14. The respiratory mask assembly as in claim 1, wherein the vent orifice comprises a plurality of semi-circular segments.

15. The respiratory mask assembly as in claim 1, wherein the vent orifice is a partial circle and partially surrounds a peninsula portion of the mask.

16. The respiratory mask assembly as in claim 1, wherein the opposed side walls provide a channel between the orifice exit of the vent orifice and an interior surface of the mask.

17. The respiratory mask assembly as in claim 16, wherein the channel has a depth at least as thick as a thickness of the mask.

18. The respiratory mask assembly as in claim 16, wherein the channel has a depth at least five times larger than a width of the orifice exit.

19. The respiratory mask assembly as in claim 16, wherein the opposed side walls have a slope of 5 degrees from an axis of the channel.

20. The respiratory mask assembly as in claim 16, wherein the opposed side walls have a slope in a range of 3 degrees to 7 degrees from an axis of the channel.

21. The respiratory mask assembly as in claim 16, wherein the channel extends outwardly from an outside surface of the mask and the channel is defined by interior walls of a ridge on the mask.

22. The respiratory mask assembly as in claim 16, wherein the channel extends inwardly of an inside surface of the mask and the channel is defined by interior walls of a groove in the mask.

23. The respiratory mask assembly as in claim 1, wherein the opposed side walls comprise a surface treatment and/or contouring.

24. The respiratory mask assembly as in claim 23, wherein the surface treatment is applied to a section of the opposed side walls adjacent the vent orifice.

25. The respiratory mask assembly as in claim 23, wherein the surface treatment comprises a roughened surface.

26. The respiratory mask assembly as in claim 23, wherein the surface contouring comprises scalloping.

27. The respiratory mask assembly as in claim 26, wherein the scalloping comprises scalloped sections aligned orthogonally to the vent orifice.

28. The respiratory mask assembly as in claim 1, wherein the washout vent comprises two washout vents provided to the shell of the mask.

29. The respiratory mask assembly according to claim 28, wherein the shell includes a receiver adapted to receive a forehead support, and the two washout vents are positioned on the shell between spaced-apart side walls of the receiver.

30. The respiratory mask assembly according to claim 28, wherein the two washout vents are positioned end to end so that they together define a reverse-S shape.

31. The respiratory mask assembly according to claim 28, wherein the two washout vents are oriented such that a line extending through a center of each of the two washout vents is perpendicular to a longitudinal axis of the shell.

32. The respiratory mask assembly according to claim 28, wherein the two washout vents are vertically aligned.

33. The respiratory mask assembly according to claim 32, wherein the two washout vents curve downwardly towards a bottom of the shell.

34. The respiratory mask assembly according to claim 32, wherein the two washout vents curve upwardly towards a top of the shell.

35. The respiratory mask assembly according to claim 28, wherein the two washout vents are horizontally aligned.

36. The respiratory mask assembly according to claim 35, wherein the two washout vents curve towards one another.

37. The respiratory mask assembly according to claim 35, wherein the two washout vents curve away from one another.

38. The respiratory mask assembly according to claim 28, wherein the two washout vents are vertically offset and the two washout vents curve towards one another.

39. The respiratory mask assembly according to claim 28, wherein the two washout vents are positioned end to end with a small overlap.

40. The respiratory mask assembly according to claim 28, wherein the two washout vents are positioned end to end with small gap therebetween so that they together define a generally S-shape.

41. The respiratory mask assembly as in claim 1, wherein the opposed side walls of the vent orifice define a channel from the interior of the mask to the orifice exit of the vent orifice.

42. The respiratory mask assembly as in claim 1, wherein the opposed side walls of the vent orifice define a gap therebetween of 0.5 millimeter to 1.0 millimeter at its narrowest width.

43. The respiratory mask assembly as in claim 42, wherein the vent orifice has a depth that is four times the narrowest width of the gap.

44. The respiratory mask assembly as in claim 1, wherein the vent orifice has a depth that is greater than a thickness of the mask.

45. The respiratory mask assembly as in claim 1, wherein the opposed side walls have surfaces shaped and/or treated to increase turbulence of gas exhausting from the interior of the mask to atmosphere.

46. The respiratory mask assembly as in claim 45, wherein the surfaces comprise scalloping with crenated edges at the orifice exit of the vent orifice.

47. The respiratory mask assembly as in claim 1, wherein the length is at least five times the width.

48. The respiratory mask assembly as in claim 1, wherein the vent orifice is elongated and extends in a plane transverse to the thickness of the solid mask section.

49. The respiratory mask assembly as in claim 1, wherein the seal comprises a sealing membrane.

50. The respiratory mask assembly as in claim 1, wherein the shell is more rigid than the seal.

51. The respiratory mask assembly as in claim 1, wherein the washout vent is provided to the shell of the mask.

* * * * *